United States Patent [19]
Johlin, Jr.

[11] Patent Number: 5,492,538
[45] Date of Patent: Feb. 20, 1996

[54] METHOD FOR TRANSFERRING THE EXIT SITE OF A CATHETER FROM THE MOUTH TO THE NOSE AND INSTRUMENTATION USEFUL THEREFOR

[76] Inventor: Frederick C. Johlin, Jr., 3517 Galway Ct., Iowa City, Iowa 52246-2765

[21] Appl. No.: 295,595

[22] Filed: Aug. 25, 1994

[51] Int. Cl.⁶ .................................................. A61M 25/00
[52] U.S. Cl. ............................. 604/264; 604/283; 600/12; 128/657; 128/899
[58] Field of Search .................................... 604/280, 283, 604/905, 264; 600/12; 128/899, 657

[56] References Cited

U.S. PATENT DOCUMENTS 3,674,014  7/1972  Tillander ................... 128/657
5,269,759  12/1993  Hernandez et al. ............ 604/280 X Primary Examiner—John D. Yasko
Attorney, Agent, or Firm—Woodward, Emhardt, Naughton, Moriarty & McNett

[57] ABSTRACT

A technique and instrumentation for transferring the exit site of a catheter, such as a nasal biliary catheter, from the mouth to the nose are described herein. The disclosed instrumentation includes a nasopharyngeal transfer catheter which has a tip of magnetically attractable material and a corresponding magnetic wand. The transfer catheter also includes a lateral hole therein near the its distal end which serves to facilitate attachment with the magnetic wand by increasing the flexibility of the transfer catheter in the direction towards the magnetic wand, while also providing access means for passing an nasal biliary catheter therethrough to effectuate the transfer of the nasal biliary catheter from the mouth to the nose. Alignment orientation and distance markings are also provided on nasalpharyngeal transfer catheter which facilitate the locating and attaching the tip of the transfer catheter to the magnetic wand.

3 Claims, 5 Drawing Sheets

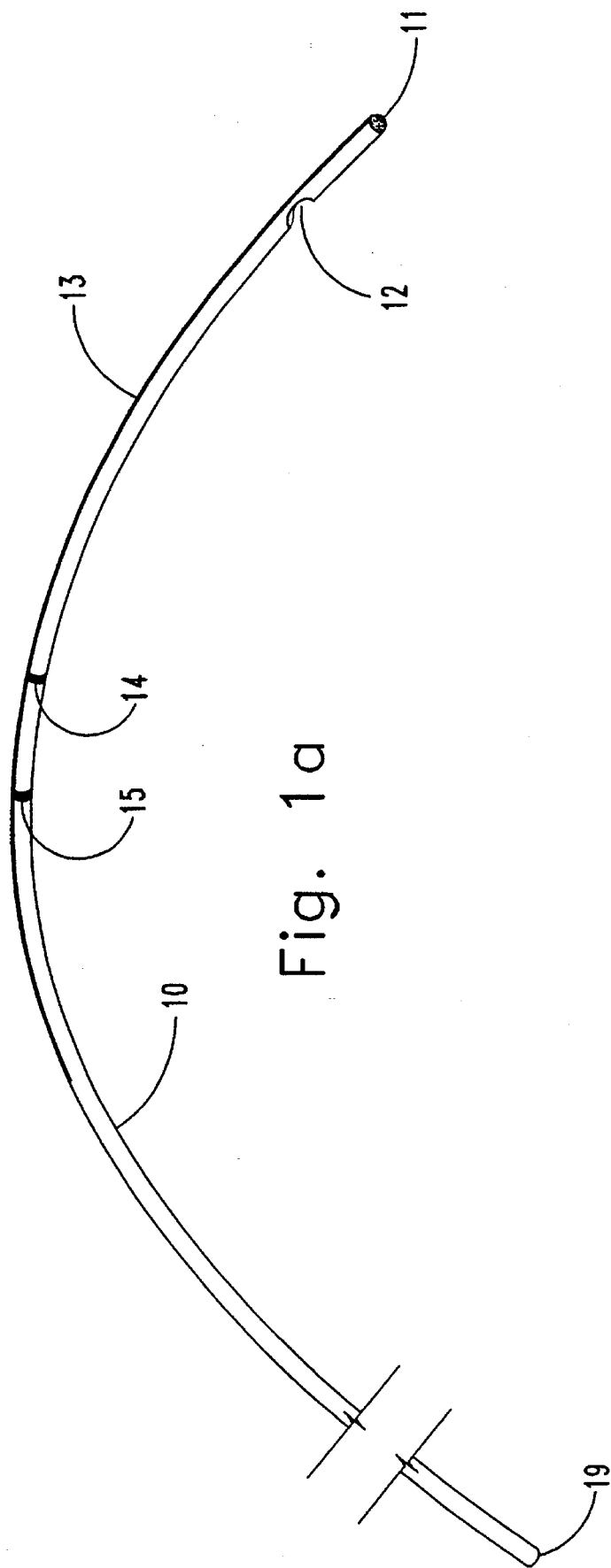

METHOD FOR TRANSFERRING THE EXIT SITE OF A CATHETER FROM THE MOUTH TO THE NOSE AND INSTRUMENTATION USEFUL THEREFOR

BACKGROUND OF THE INVENTION

1. Field of the Invention

This invention relates to facilitating the transfer of the exit site of a catheter from the mouth to the nose. Devices that typically require this assistance include nasobiliary stents and endoscopically placed drainage and feeding devices. A device of the present invention could be useful in other procedures as well, such as, for example, the stabilization of nasally placed devices by a maneuver known as "bridling."

2. Description of the Prior Art

It is sometimes desirable to place a catheter into the biliary system, pancreas, or upper gastrointestinal tract through the mouth. After the catheter has been endoscopically implanted, the proximal end of the catheter is stationed out of the mouth of the patient. It is preferable, however, to transfer the exit site of the catheter to the nose, which is much more convenient and comfortable for the patient and reduces the risk that the catheter will be damaged by mastication. The transfer procedure is typically accomplished with the use of a well-lubricated nasopharyngeal tube which is advanced through the nostril and down the pharynx. The endoscopist then grasps the tip of the nasopharyngeal tube in the posterior oropharynx region with his or her index finger (or sometimes with forceps) and pulls it out through the mouth. The tip of the catheter is then threaded through a hole at or near the oral end of the nasopharyngeal tube and advanced until it exits through the nasal end of the tube. The nasopharyngeal tube is then slowly pulled out through the nostril, bringing the catheter along with it.

Problems are encountered in this procedure, however, in the process of locating, grasping, and pulling the nasopharyngeal tube out through the mouth once it has been advanced into the posterior oropharynx region. This is at least partly because the nasopharyngeal tube can sometimes be difficult to locate and grasp, particularly if the physician or assistant performing the maneuver has shorter fingers or the patient has an unusually small mouth. On occasion, the grasping digit has been bitten by the patient while trying to locate and pull the nasopharyngeal tube out through the mouth. The alternative of using a grasping instrument such as forceps, on the other hand, means that the posterior oropharynx region must be probed blindly to locate and securely grasp the nasopharyngeal tube for extraction. Without the benefit of a visual or tactile aid, a fair amount of time and effort is often required before the nasopharyngeal tube can be successfully extracted from the patient with forceps. And, as with the experience of having a hand reach into the back of your mouth, this blind probing with a foreign instrument into a sensitive region of the body can be uncomfortable and unpleasant for the patient and can result in trauma to the pharyngeal tissues. Both patient and physician would benefit from an improved way of accomplishing the transfer of a catheter from the mouth to the nose. Such an improved procedure would enable the physician to easily locate and extract the nasopharyngeal transfer device, and would do so in a way that would alleviate the unpleasantness and risks of the experience to the patient.

SUMMARY OF THE INVENTION

The present invention provides a new and safer way of transferring the proximal end of a catheter, such as a nasal biliary catheter, from the mouth to the nose, and provides new instrumentation which is designed for accomplishing this transfer. Such instrumentation, as described herein, enables the physician to be able to easily locate and extract a nasopharyngeal transfer catheter after it has been inserted into the nostril and through the nasal passageway and into the posterior oropharyngeal region. With the present invention, a physician can perform the procedure of transferring the exit site of a catheter from the mouth to the nose without risking injury from being bitten, and while also removing much of the unpleasantness and risk of the experience to the patient.

As described herein, instrumentation for the present invention includes a specially constructed nasopharyngeal transfer catheter with a tip of magnetically attractable material and a corresponding magnetic wand. A lateral hole which is formed near the distal end of the transfer catheter which both serves to facilitate attachment and provides access for passing a catheter therethrough as part of the transfer procedure. Orientation and distance markings are also provided which facilitate the locating and attaching of the transfer catheter tip to the magnetic wand.

It is an object of the present invention to provide a safe and easy way to transfer the exit site of a catheter from the mouth to the nose, and to do so in a way which is less traumatic for the patient. A full appreciation of this invention and its benefits can be drawn from a review of the following detail specification and claims.

BRIEF DESCRIPTION OF THE DRAWINGS

FIG. 1a is a partially fragmented side elevational view of a nasopharyngeal transfer catheter which is specially constructed for use with the present invention. FIG. 1b is a side elevational view of a magnetic wand which is used with the present invention to locate and extract the nasopharyngeal transfer catheter of FIG. 1a out through the mouth after the transfer catheter has been passed in the nose and through the sinus passageways into the posterior oropharynx region.

In FIG. 2a, nasopharyngeal transfer catheter 10 has been passed through the nasal passageways of the patient and in the posterior oralpharyngeal region, and magnetic wand 20 has been inserted through the mouth toward this region. FIG. 2b shows transfer catheter 10 having been magnetically attracted towards wand 20 to form an attachment therewith. In FIG. 2c, transfer catheter 20 has been pulled out through the mouth by magnetic wand 20, and nasal biliary catheter 30 has been advanced through lateral slot 12 and out through the proximal end 19 of nasopharyngeal transfer catheter 10.

DESCRIPTION OF THE PREFERRED EMBODIMENT

Figure 2A:
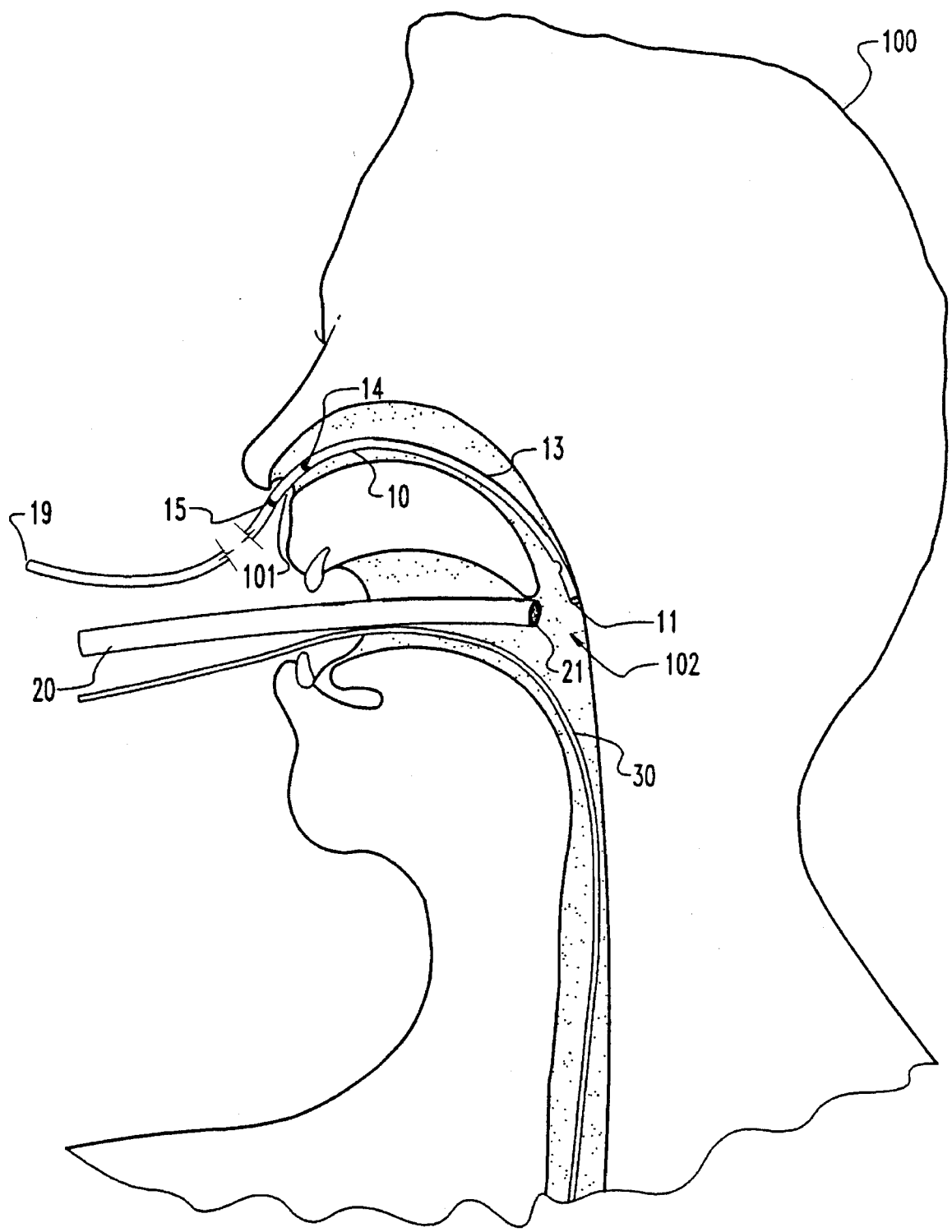
FIGS. 2a–c are side cross-sectional views of the head and neck portion of a patient 100, and illustrating the nasal-oral-pharyngeal passageways therein and showing a nasal biliary catheter 30 which has been endoscopically placed into the patient.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, there is provided nasal transfer catheter 10 and magnetic wand 20 which are constructed to accomplish a secure attachment in the posterior oropharyngeal region with ease and with minimal resistance. For this purpose, wand 20 includes a high gauss magnet (for example, an alloy type magnet such as Alnico or reodynium-ion-boron) 21 at its distal tip and tip 11, formed at the end of tubular transfer catheter 10, is made of a suitably magnetized material that will attach to magnet 21. Two distance markings 14 and 15 have been placed on transfer catheter 10 in the form of rings at 12 and 14 cm. distances, respectively, from distal tip 11 of transfer catheter 10. Distance markings have been placed, in distance to distal tip 11, to approximate the range of distances normally expected to be encountered in an adult patient between the nasolabial fold and his/her posterior pharynx.

Transfer catheter 10 additionally has an alignment orientation marking in the form of a long line 13 which is to be oriented cephalad, and transfer catheter 10 is also formed in a curvature along its length to facilitate advancement through the nasal passageway. When properly allinged with the aid of allignment orientation marking 13, this curved structure allows transfer catheter 10 to easily follow the arc of the palate and pass into the posterior pharynx with less effort and trauma. Lateral hole 12, which is disposed oppositely of orientation mark 13 on transfer catheter 10, is oriented anteriorly to enhance the flexibility of transfer catheter 10 near its distal tip and to thus facilitate the forming of the desired attachment with magnetic wand 20.

Figure 2B:
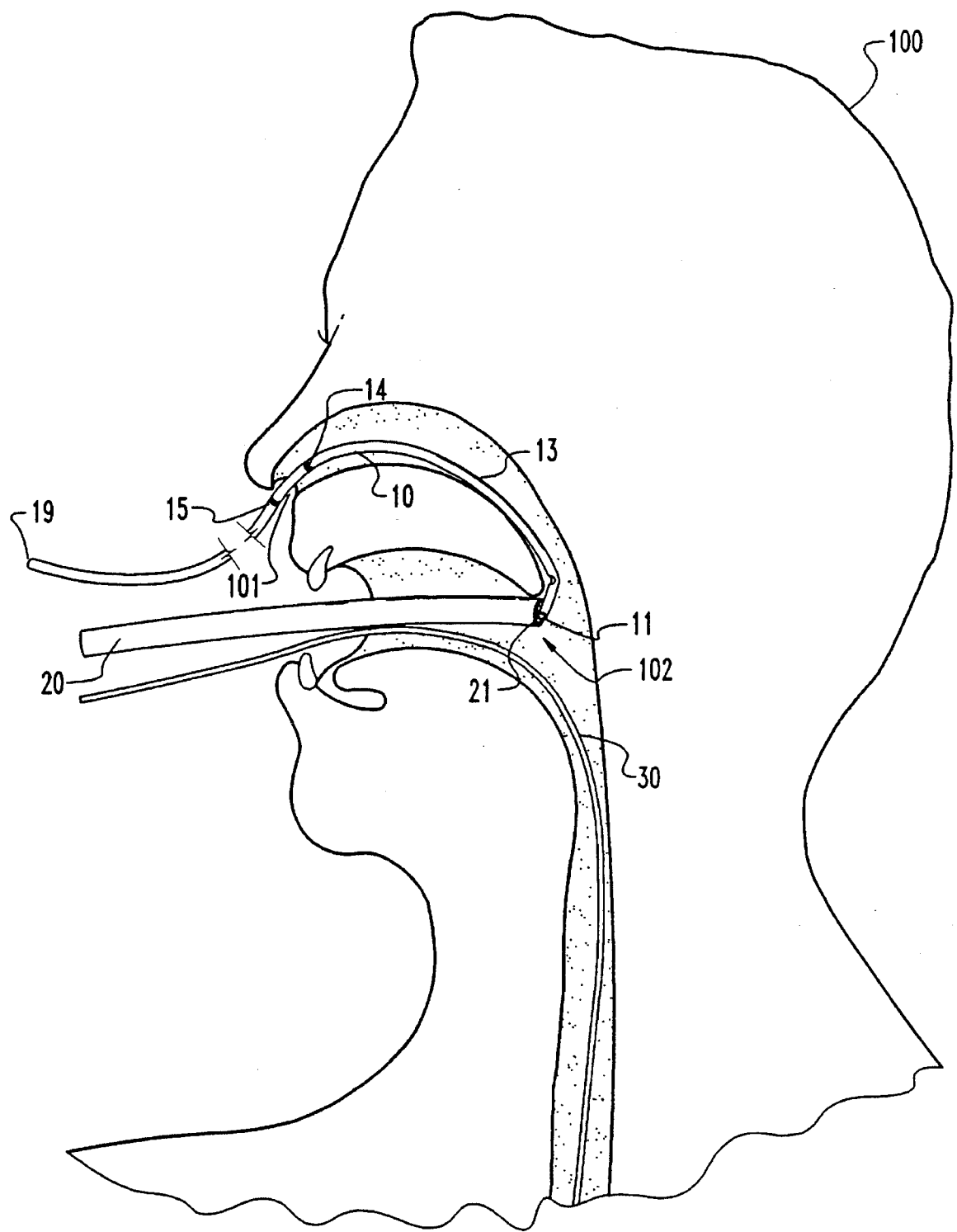
Figure 2C:
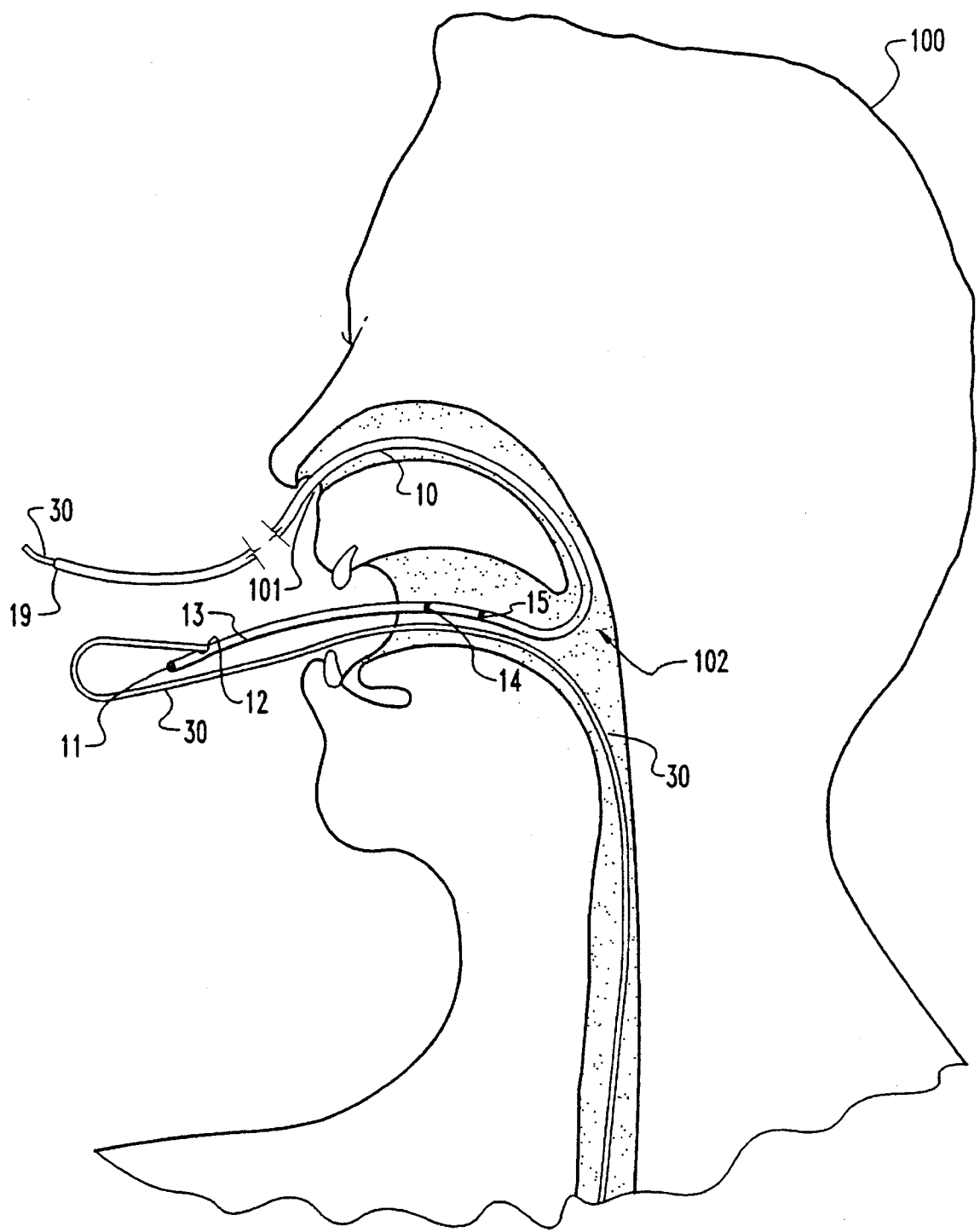
Figure 3:
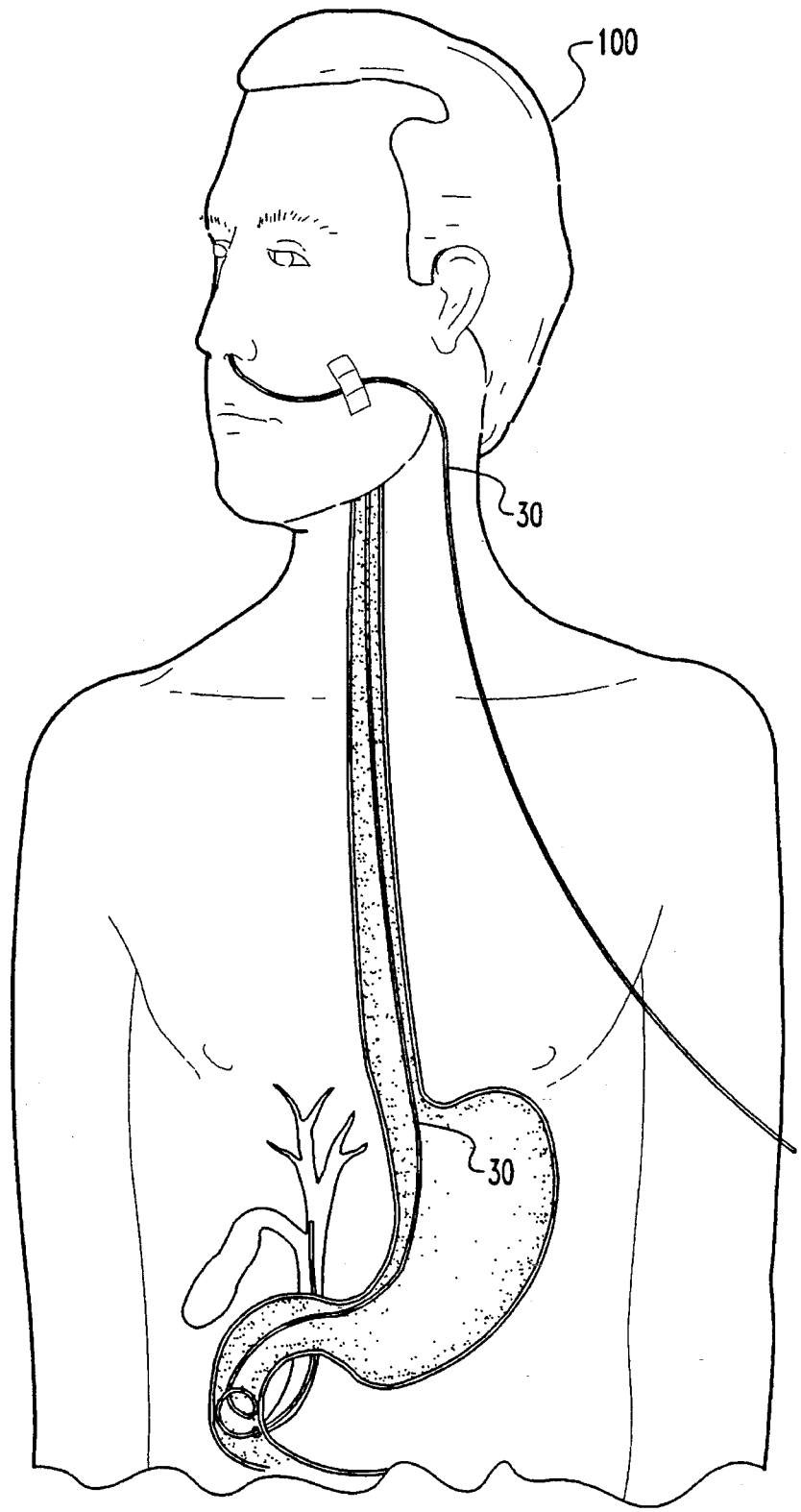
FIG. 3 is an illustration of patient 100 with the transfer procedure having been completed and with nasal biliary catheter 30 in fully in place for use.

FIGS. 2a–c are side cross-sectional views of the head and neck portion of a patient 100, and illustrating the nasal-oralpharyngeal passageways therein and showing a nasal biliary catheter 30 which has been endoscopically placed into a patient. As shown in FIG. 2a, nasopharyngeal transfer catheter 10 has been advanced through the nasal passageways so that the first black ring 14 is no longer showing, and magnetic wand 20 has been introduced into the mouth of patient 100 and in toward the posterior oralpharyngeal region 102. Preferably, magnetic wand 20 should be kept to one side and be positioned about 5 mm. away from the posterior pharynx.

If wand 20 does not engage transfer catheter 10 after wand 20 and transfer catheter 10 have been advanced as shown in FIG. 2a, the physician should then slowly advance transfer catheter 10 further until the second distance ring 15 is touching nasolabial fold 101. Magnet 21 will then capture transfer catheter 10 in most adults. In children, the distance is more variable, thus requiring a visual estimation on the part of the physician. FIG. 2b shows transfer catheter 10 having been magnetically attracted towards wand 20 to form an attachment therewith. In FIG. 2b, it is also seen how lateral slot 12 enhances the flexibility of catheter 10 towards magnetic wand 20, thereby facilitating the formation of the attachment.

In FIG. 2c, transfer catheter 10 has been pulled out through the mouth by magnetic wand 20, and nasal biliary catheter 30 has been advanced through lateral slot 12 and out through the proximal end 19 of nasopharyngeal transfer catheter 10. So configured, transfer catheter 10 and nasal biliary catheter 30 can be pulled out together through the nasal passageways and out through the nose to effectuate the desired transfer of nasal biliary catheter 30 to a nasal exit site.

It is preferred to use a high gauss force magnet 21 in magnetic wand 20 to ensure that catheter 10 is gripped with enough force to engage and drag catheter 10 out through the mouth. It is to be appreciated, though, that the invention may be practically performed with magnets of lesser strength. Also, a magnet could alternatively be placed on the distal tip of transfer catheter 10, with magnetically attractive material placed on the distal tip of wand 20, or two magnets, with oppositely disposed facing polarities, could be used as well.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. Instrumentation for transferring the proximal end of a catheter from the mouth to the nose, said instrumentation comprising:

a nasopharyngeal transfer catheter, said nasopharyngeal transfer catheter being generally tubular in structure and including a distal tip portion formed at least partially by magnetically attractable material, said transfer catheter being sized for insertion into a nostril of a patient and advanceable through the nasal passageway to position said distal tip portion of said transfer catheter in the posterior oralpharyngeal region; and a wand, said wand including a distal tip portion formed at least partially by magnetically attractable material, said wand being sized for insertion into the mouth of a patient and advanceable therein to position said distal tip portion of said wand in the posterior oralpharyngeal region;

the magnetically attractable material in one of said distal tip portion of said transfer catheter and said distal tip portion of said wand being a magnet of sufficient strength to attract and attach to the magnetically attractable material in the other of said two distal tip portions when said two distal tip portions are both positioned in the posterior oralpharyngeal region, with the formed magnetic attachment being strong enough to enable said transfer catheter to be pulled out through the mouth by said wand.

2. The instrumentation of claim 1 in which said transfer catheter further has formed therein a lateral hole in proximity to said distal tip portion thereof providing access for passing a catheter through said transfer catheter while also enhancing the flexibility thereof at the distal tip portion of said transfer catheter in the direction of said lateral hole.

3. The instrumentation of claim 2 wherein said transfer catheter further includes an orientation marking along at least a portion of the length thereof to thereby provide a visual aid to facilitate the anterior allignment of said lateral hole when said transfer catheter has been advanced through the nasal passageway and into the posterior oralpharyngeal region.

* * * * *